US009770333B2

(12) United States Patent
Perkins et al.

(10) Patent No.: US 9,770,333 B2
(45) Date of Patent: Sep. 26, 2017

(54) METHODS, DEVICES AND SYSTEMS FOR TREATING VENOUS INSUFFICIENCY

(71) Applicant: Medtronic Vascular, Inc., Santa Rosa, CA (US)

(72) Inventors: D. H. Perkins, Santa Rose, CA (US); Rany Huynh, Charleston, CA (US); Dustin Thompson, Santa Rosa, CA (US); Nasser Rafiee, Andover, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 234 days.

(21) Appl. No.: 14/056,740

(22) Filed: Oct. 17, 2013

(65) Prior Publication Data

US 2014/0046424 A1 Feb. 13, 2014

Related U.S. Application Data

(62) Division of application No. 12/054,553, filed on Mar. 25, 2008, now abandoned.

(51) Int. Cl.
*A61B 17/12* (2006.01)
*A61F 2/24* (2006.01)
*A61F 2/95* (2013.01)

(52) U.S. Cl.
CPC .............. *A61F 2/2475* (2013.01); *A61F 2/95* (2013.01); *A61B 17/12013* (2013.01); *A61F 2/2445* (2013.01)

(58) Field of Classification Search
CPC .............. A61F 2/2475; A61F 2002/249; A61F 2002/068; A61F 6/20–6/208; A61B 17/12; A61B 17/12013; A61B 17/12036; A61B 17/128; A61B 17/1285; A61B 17/1259; A61M 2025/1054
USPC .............. 606/1, 108, 195, 200; 128/842–843, 128/830–831, 835; 623/1.11–1.12, 23.64, 623/23.68–23.7; 604/173; 600/37
See application file for complete search history.

(56) References Cited

U.S. PATENT DOCUMENTS

| | | | |
|---|---|---|---|
| 5,824,061 A | 10/1998 | Quijano et al. | |
| 5,964,806 A * | 10/1999 | Cook | A61B 17/062 600/30 |
| 6,071,292 A | 6/2000 | Makower et al. | |
| 6,241,763 B1 | 6/2001 | Drasler et al. | |
| 6,299,637 B1 | 10/2001 | Shaolian et al. | |
| 6,319,281 B1 | 11/2001 | Patel | |

(Continued)

OTHER PUBLICATIONS

Garcia-Rinaldi et al. "Implantation of Cryopreserved Allograft Pulmonary Monocusp Patch" Clinical Investigation, Tex Heart Inst J 2002;29:92-9.

*Primary Examiner* — Victor Nguyen
*Assistant Examiner* — Jonathan Hollm

(57) ABSTRACT

Methods and systems for improving the competency of a venous valve wherein one or more compressor(s) (e.g., space occupying material(s) or implantable device(s)) is/are delivered to one or more location(s) adjacent to a venous valve to compress the venous valve in a manner that causes one or both leaflets of the valve to move toward the other, thereby improving closure or coaptation of the valve leaflets. The compressor(s) may be delivered by an open surgical approach, by a direct percutaneous approach or by a transluminal catheter-based approach.

10 Claims, 11 Drawing Sheets

(56) References Cited

U.S. PATENT DOCUMENTS

| | | | |
|---|---|---|---|
| 6,375,666 B1* | 4/2002 | Mische | A61M 25/10 606/198 |
| 6,458,153 B1 | 10/2002 | Bailey et al. | |
| 6,562,068 B2 | 5/2003 | Drasler et al. | |
| 6,591,838 B2* | 7/2003 | Durgin | A61B 17/00234 128/898 |
| 6,602,241 B2 | 8/2003 | Makower et al. | |
| 6,652,578 B2 | 11/2003 | Bailey et al. | |
| 6,716,241 B2 | 4/2004 | Wilder et al. | |
| 6,902,576 B2 | 6/2005 | Drasler et al. | |
| 6,932,838 B2 | 8/2005 | Schwartz et al. | |
| 6,958,076 B2 | 10/2005 | Acosta et al. | |
| 7,007,698 B2 | 3/2006 | Thornton | |
| 7,018,408 B2 | 3/2006 | Bailey et al. | |
| 7,396,540 B2* | 7/2008 | Chu | A61M 5/00 424/423 |
| 2001/0011189 A1 | 8/2001 | Drasler et al. | |
| 2001/0018592 A1 | 8/2001 | Schaller et al. | |
| 2001/0021872 A1 | 9/2001 | Bailey et al. | |
| 2002/0148475 A1* | 10/2002 | Johnson | A61B 17/12036 128/897 |
| 2002/0177894 A1 | 11/2002 | Acosta et al. | |
| 2003/0023300 A1 | 1/2003 | Bailey et al. | |
| 2003/0055492 A1 | 3/2003 | Shaolian et al. | |
| 2003/0130727 A1 | 7/2003 | Drasler et al. | |
| 2003/0171802 A1 | 9/2003 | Wilder et al. | |
| 2004/0024447 A1 | 2/2004 | Haverich | |
| 2004/0106976 A1 | 6/2004 | Bailey et al. | |
| 2004/0133267 A1 | 7/2004 | Lane | |
| 2004/0193253 A1 | 9/2004 | Thorpe et al. | |
| 2004/0199155 A1* | 10/2004 | Mollenauer | A61B 18/08 606/27 |
| 2004/0215339 A1 | 10/2004 | Drasler et al. | |
| 2005/0070993 A1* | 3/2005 | Boekstegers | A61F 2/01 623/1.25 |
| 2005/0137676 A1 | 6/2005 | Richardson et al. | |
| 2005/0137681 A1 | 6/2005 | Shoemaker et al. | |
| 2006/0142789 A1* | 6/2006 | Lehman | A61B 17/00234 606/153 |
| 2006/0167543 A1 | 7/2006 | Bailey et al. | |
| 2006/0178729 A1 | 8/2006 | Thielen et al. | |
| 2006/0178730 A1 | 8/2006 | Hill et al. | |
| 2006/0247762 A1 | 11/2006 | Acosta et al. | |
| 2006/0282157 A1 | 12/2006 | Hill et al. | |
| 2007/0014784 A1 | 1/2007 | Nayak et al. | |
| 2007/0050013 A1 | 3/2007 | Gross | |
| 2007/0067021 A1 | 3/2007 | Haverkost et al. | |
| 2007/0112423 A1 | 5/2007 | Chu | |
| 2007/0129788 A1 | 6/2007 | Drasler et al. | |
| 2007/0265699 A1 | 11/2007 | Grewe et al. | |

* cited by examiner

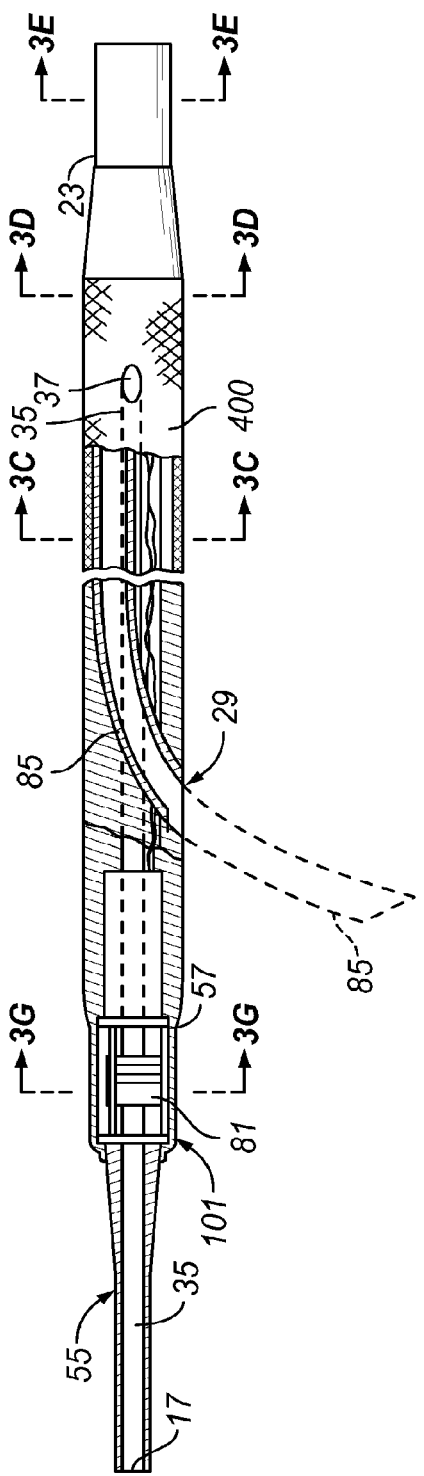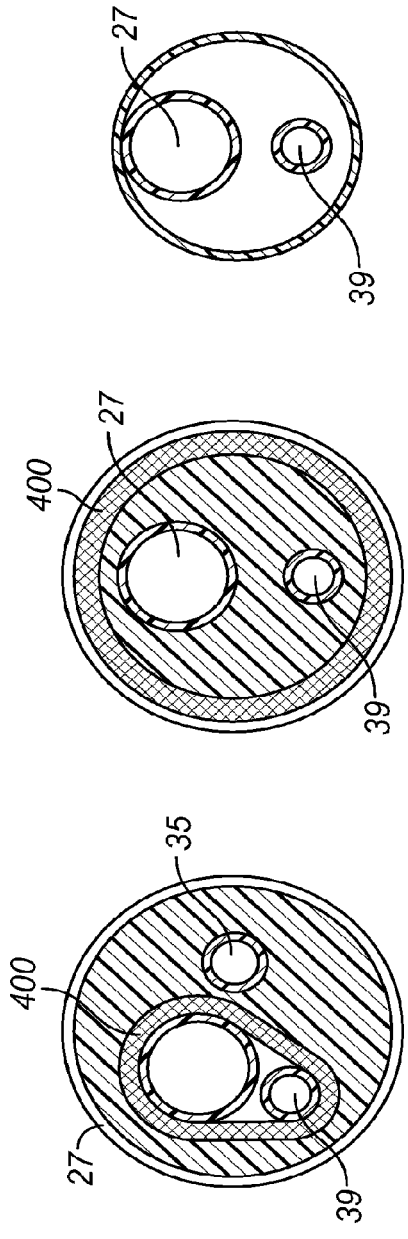
FIG. 3B
FIG. 3C
FIG. 3D
FIG. 3E

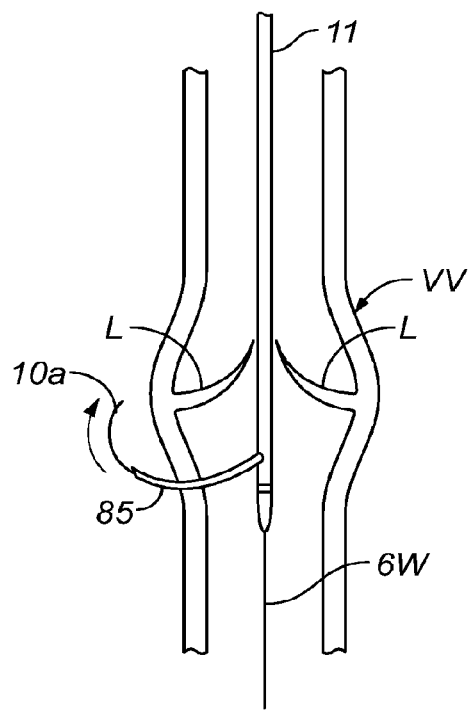
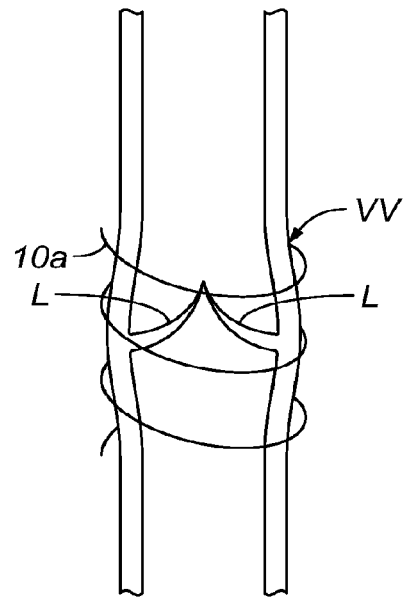
*FIG. 5A*  *FIG. 5B*
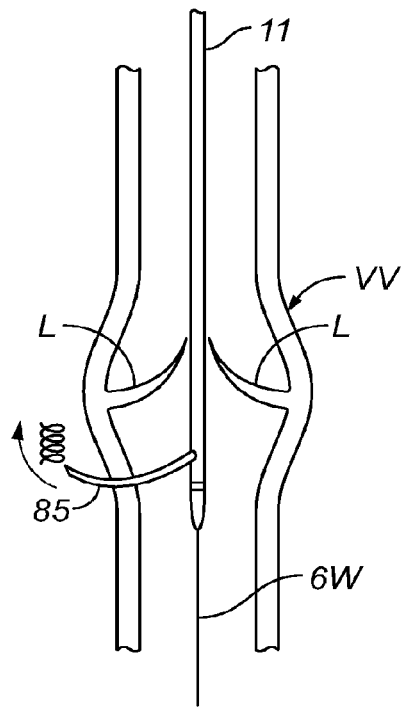
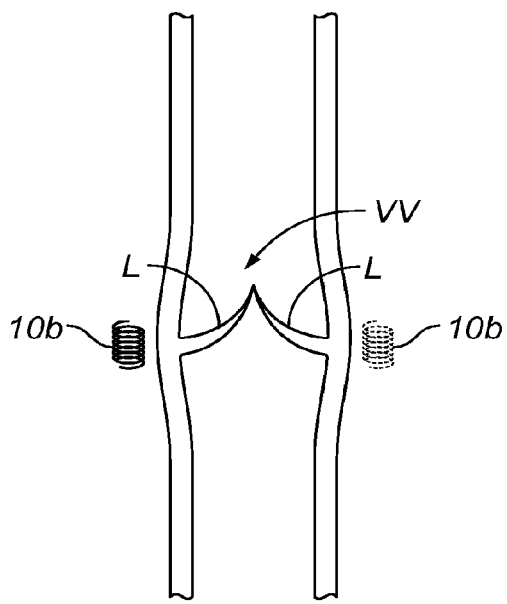
*FIG. 6A*  *FIG. 6B*

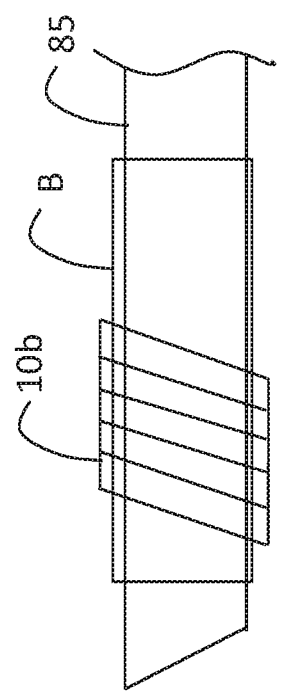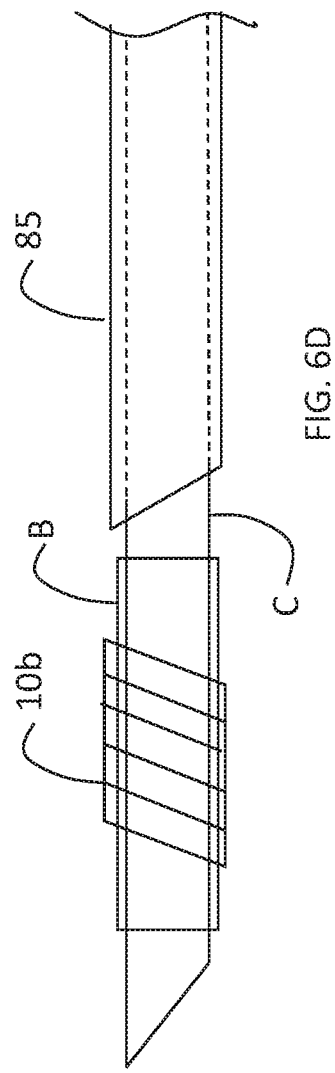

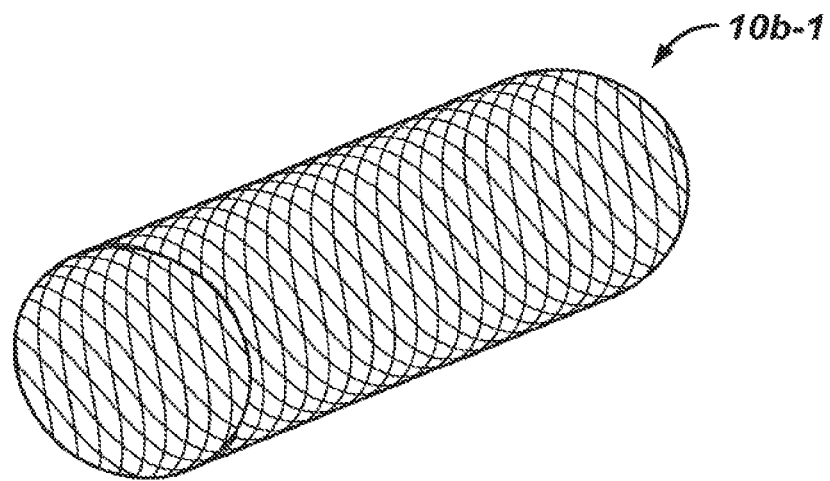
FIG. 6E
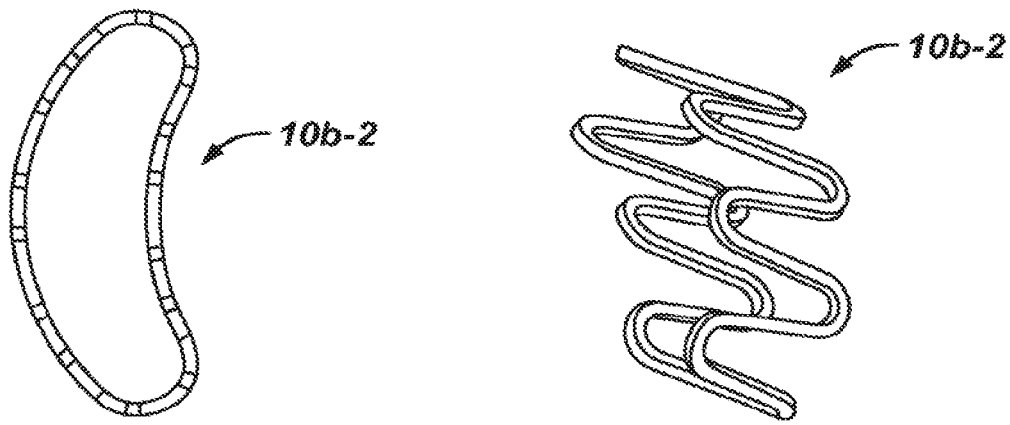
FIG. 6F
FIG. 6G

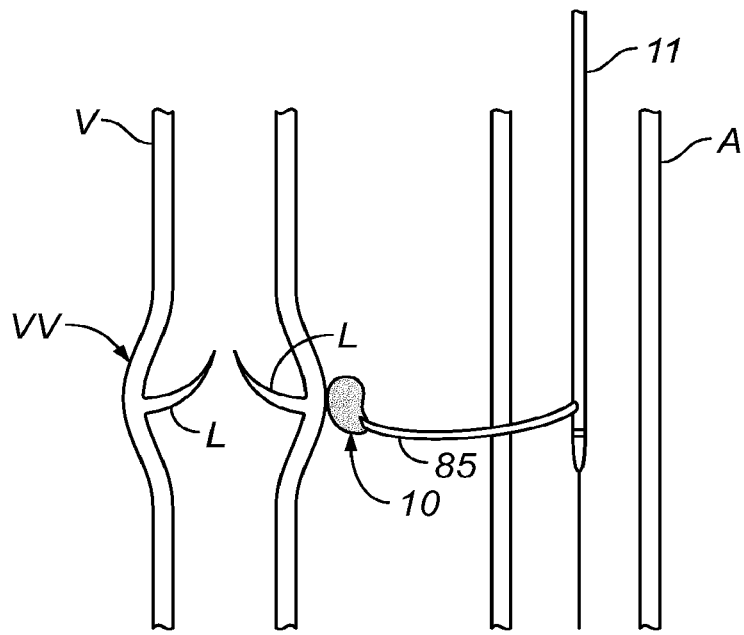
FIG. 7
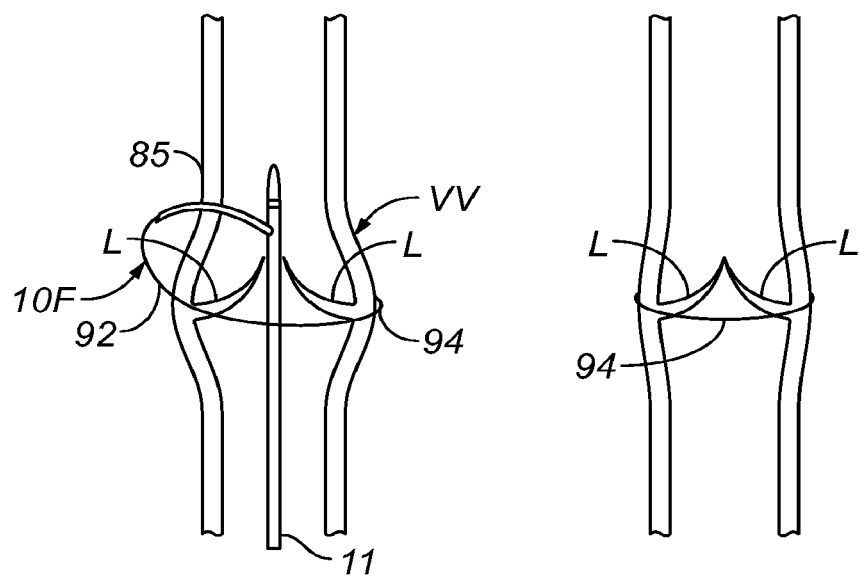
FIG. 8A  FIG. 8B

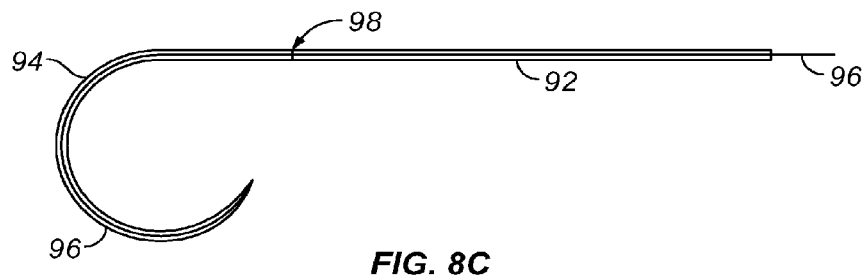
FIG. 8C
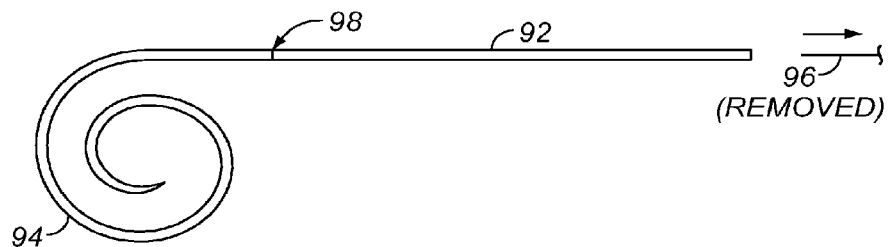
FIG. 8D
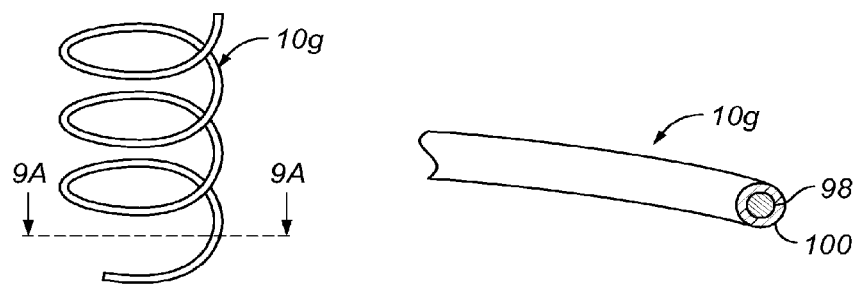
FIG. 9
FIG. 9A

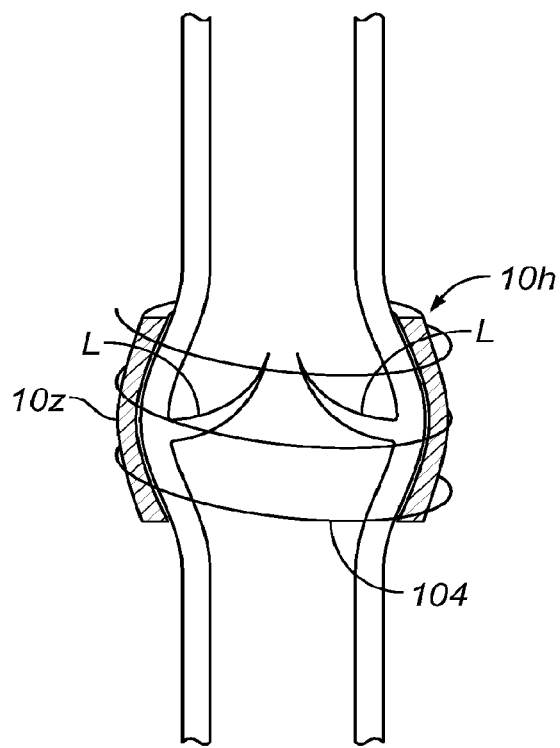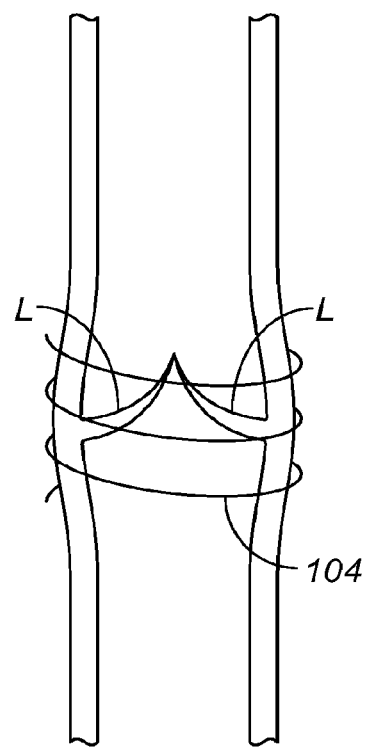
FIG. 10  FIG. 10A

METHODS, DEVICES AND SYSTEMS FOR TREATING VENOUS INSUFFICIENCY

RELATED APPLICATION

This is a division of copending U.S. patent application Ser. No. 12/054,553 filed Mar. 25, 2008, the entire disclosure of which it expressly incorporated herein by reference.

FIELD OF THE INVENTION

The present invention relates generally to medical devices and methods, and more particularly to devices and methods for treating incompetent venous valves.

BACKGROUND

The venous vasculature of the lower extremities includes superficial veins (such as the lesser and greater saphenous veins and their tributaries), deep veins (such as the anterior tibial, posterior tibial, peroneal, popliteal, deep femoral, superficial femoral, and iliac veins) and perforator veins (veins which connect the superficial veins to the deep veins). All veins of the lower extremities have valves which prevent the blood from falling (refluxing) back down the leg and help to keep the venous return blood flowing only in one direction, i.e., toward the heart. Each venous valve consists of two leaflets that move apart from one another as blood flows up the leg toward the heart and, thereafter, move toward one another so that they come into contact (i.e., coaptation) with each other, thereby preventing blood from backflowing in a direction away from the heart.

The congenital absence or incompetence of the venous valves results in a condition known as Chronic Venous Insufficiency (CVI). In CVI, venous blood tends to pool in the lower leg. This can cause distention of the veins (i.e., varicose veins), edema or swelling, pain, skin discoloration and, in severe cases, skin ulcers. In cases where the incompetent valves are located in superficial or perforator veins, the problem can be remedied by surgical removal of the affected veins. However, when the incompetent venous valves are located in deep veins, other treatment approaches must be considered because the deep veins are generally essential and cannot be removed.

The prior art has included various means for treating CVI, ranging from palliative techniques such as the wearing of contrictive stockings to surgical procedures such as vein removal, vein bypass, valvuloplasty or replacement of the affected venous valve with a transplanted homograft valve from elsewhere in the patient's venous vasculature or with a prosthetic valve. Examples of devices and techniques for treatment of incompetent venous valves are described in U.S. Pat. Nos. 7,018,408, 6,958,076, 6,902,576, 6,716,241, 6,652,578, 6,562,068, 6,458,153, 6,319,281, 6,299,637, 6,241,763 and 5,824,061 and United States Patent Application Publications Nos. 20070265699, 20070129788, 20070112423, 20070067021, 20070050013, 20060282157, 20060247762, 20060178730, 20060178729, 20060167543, 20050137681, 20050137676, 20040215339, 20040193253, 20040106976, 20040024447, 20030171802, 20030130727, 20040133267, 20030055492, 20030023300, 20020177894, 20010021872 and 20010011189.

In particular, United States Patent Application Publication No. 20040133267 (Lane) describes external stents to render incompetent venous valves competent. In one embodiment, the external stent comprises an inelastic bio-compatible cuff that encircles the venous valve cusps decreasing the internal diameter of the vein wall to allow apposition of the cusps and create improved competence of the valve.

There remains a need in the art for the development of new devices and methods for repairing incompetent venous valves.

SUMMARY OF THE INVENTION

The present invention provides a method and system for improving the competency of a venous valve wherein a compressor (e.g., a space occupying material or implantable device) is delivered at one or more location(s) adjacent to the venous valve to cause one or both leaflets of the valve to move toward the other, thereby improving closure or coaptation of the valve leaflets.

In accordance with one embodiment of the invention, a compressor comprising a quantity of space occupying material is injected into tissue at one or more location(s) adjacent to the venous valve. This space occupying material compresses the venous valve in a manner that cause one or both leaflets of the valve to move toward the other, thereby improving closure or coaptation of the valve leaflets.

Further in accordance with another embodiment of the invention, a compressor comprising one or more implantable device(s) is/are implanted at one or more location(s) adjacent to the venous valve. Such implanted device(s) compresses the venous valve in a manner that causes one or both leaflets of the valve to move toward the other, thereby improving closure or coaptation of the valve leaflets. Various types of implantable device may be used, including but not limited to expandable or self expanding members, balloons or inflatable members, springs, etc.

Still further in accordance with the invention, the compressor (e.g., space occupying material or implantable device(s)) may be delivered to the desired location(s) adjacent to the venous valve by any suitable means including by open surgery (e.g, directly through an incision which exposes the area near the venous valve), by direct percutaneous injection/introduction or transluminally (e.g., using catheter(s) advanced through the vasculature to or near the site of the venous valve). In one example of a transluminal approach, a catheter having a tissue penetrator (e.g., an advanceable needle) may be advanced into the lumen of the vein in which the insufficient venous valve is located or an adjacent blood vessel near the incompetent venous valve. The penetrator may then be advanced from the catheter to a desired position adjacent to the venous valve. Thereafter, the compressor (e.g., space occupying material or implantable device(s)) may be delivered from, through or over the penetrator to the desired location adjacent the venous valve such that the compressor compresses the venous valve in a manner that causes one or both leaflets of the venous valve to move closer to the other, thereby improving closure of the leaflets and competency of the valve. Thereafter, the penetrator may be retracted into the catheter and the catheter may be removed.

Further aspects, elements, embodiments, objects and advantages of the present invention will be appreciated by those of skill in the relevant art upon reading the detailed description and examples set forth herebelow.

BRIEF DESCRIPTION OF THE DRAWINGS

FIG. 3B is an enlarged, partially fragmentary, elevational view of a distal portion of the tissue penetrating catheter device seen in FIG. 3A.

FIG. 3C is a non-fragmented cross sectional view through line 3C-3C of FIG. 3B.

FIG. 3D is a cross sectional view through line 3D-3D of FIG. 3B.

FIG. 3E is a cross sectional view through line 3E-3E of FIG. 3B.

FIGS. 5A and 5B are schematic diagrams showing steps in a particular embodiment of the method of the present invention wherein a compressor comprising a helical wire is advanced around the venous valve so as to cause the desired compression of the venous valve.

FIGS. 6A-6D are schematic diagrams showing steps in a particular embodiment of the method of the present invention wherein a compressor comprising one or more expandable implantable device(s) is/are implanted adjacent to the venous valve so as to cause the desired compression of the venous valve.

FIG. 6E is a perspective view of a compressor of the present invention which comprises a radially expandable tubular member.

FIG. 6F is a top view of another compressor of the present invention which comprises an implantable spring device formed of a zig-zag member which forms an indented ring.

FIG. 6G is a perspective view of the implantable spring device of FIG. 6F.

FIG. 7 is a schematic diagram of a method of the present invention wherein a tissue penetrating catheter is positioned in an artery and used to deliver a compressor to a location adjacent to a venous valve of a neighboring vein.

FIG. 8A is a schematic diagram of a step in a method of the present invention wherein a tissue penetrating catheter is positioned in an artery and used to deliver a compressor comprising a clip device which contracts around a venous valve to improve coaptation of the leaflets of the venous valve.

FIG. 8A is a schematic diagram of another step in the method of FIG. 8A showing the clip device contracted around the venous valve after the tissue penetrating catheter has been removed.

FIGS. 8C and 8D are side views of the clip device used in the method of FIGS. 8A and 8B. In FIG. 8A, a wire mandrel is inserted into the device causing the clip member to have a first curved configuration which allows it to safely advance around the exterior of a venous valve. In FIG. 8D, the wire mandrel has been removed, allowing the clip member to assume a second curved or coiled configuration which causes it to compress the venous valve thereby improving closure of the valve leaflets.

FIG. 9 is a side view of a venous valve compressor device of the present invention which comprises a helical wire that is biased to a tight helical configuration and a biodegradable polymer covering on the wire that is biased to a looser helical configuration so that the device will initially advance around the valve and will subsequently contract as the biodegradable covering degrades, thereby compressing the venous valve.

FIG. 9A is a cross sectional view through line 9A-9A of FIG. 9.

FIG. 10 is a schematic diagram of an artery having a venous valve compression system of the present invention positioned around the valve, such compression system comprising a biodegradable spacer surrounded by a helical wire compressor, the helical wire compressor being biased to a diameter that is smaller than the outer diameter of the spacer and will compress the venous valve after the biodegradable spacer has degraded.

FIG. 10A is a schematic diagram showing the helical wire compressor of FIG. 10 after the biodegradable spacer has degraded and the helical wire compressor has contracted to its smaller diameter, thereby compressing the venous valve.

DETAILED DESCRIPTION AND EXAMPLES

The following detailed description and the accompanying drawings are intended to describe some, but not necessarily all, examples or embodiments of the invention. The contents of this detailed description and accompanying drawings do not limit the scope of the invention in any way.

Figure 1:
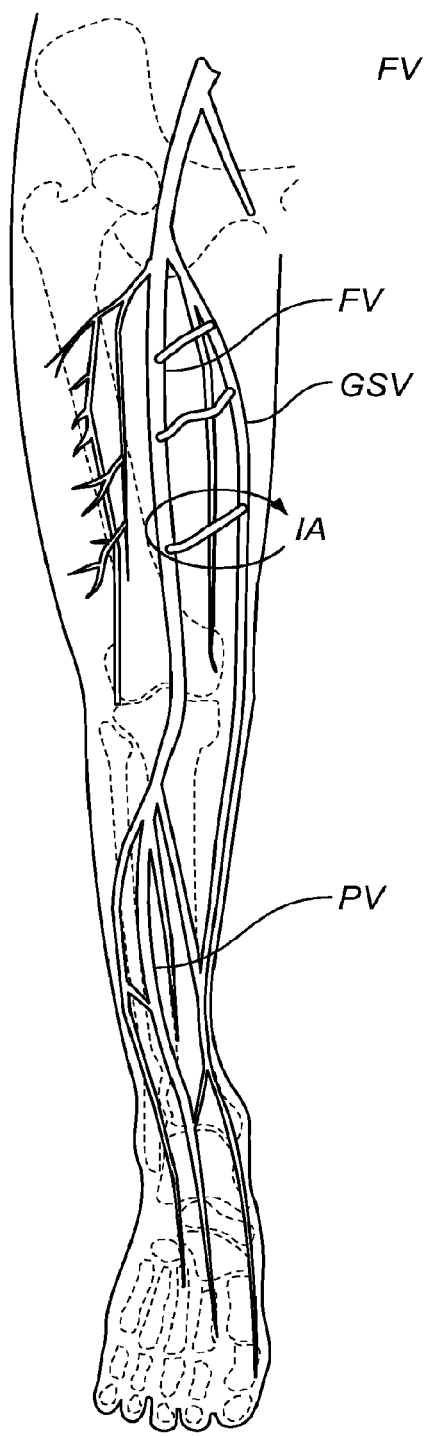
FIG. 1 is a diagram of a human leg showing various veins of the leg.
Figure 1A:
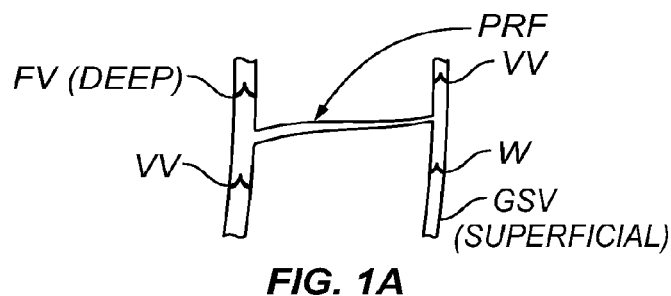
FIG. 1A is an enlarged view of area 1A of FIG. 1.

Referring to the accompanying drawings, FIG. 1 shows various veins of the human leg including the femoral vein FV, great saphenous vein GSV and popliteal vein PV. In the enlarged view of FIG. 1A, it can be appreciated that the femoral vein FV is an example of a deep vein, the great saphenous vein is an example of a superficial vein and smaller perforator veins PRF run between the deep veins and superficial veins.

Figure 1B:
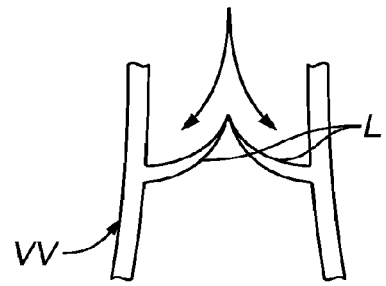
FIG. 1B is a transverse sectional diagram of a vein having a competent venous valve in its closed position, with normal coaptation of the valve leaflets.

FIG. 1B shows a normal venous valve V V in a closed position such that the leaflets L of the venous valve V V meet or coapt with one another, thereby blocking retrograde flow of blood through the venous valve V V.

Figure 1C:
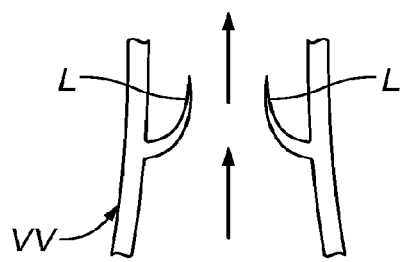
FIG. 1C is a transverse sectional diagram of a vein having a competent venous valve in its open position.

FIG. 1C shows a normal venous valve V V in an open position such that the leaflets L of the valve are separated from one another allowing venous blood to flow through the venous valve V V toward the heart.

Figure 1D:
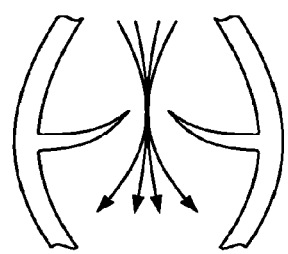
FIG. 1D is a transverse sectional diagram of a vein having an incompetent venous valve in its closed position, showing non-coaptation of the valve leaflets.

FIG. 1D shows an incompetent venous valve V V in a closed position such that the leaflets L of the valve do not fully coapt with one another, thereby allowing retrograde flow of blood through the valve V V.

Figure 2A:
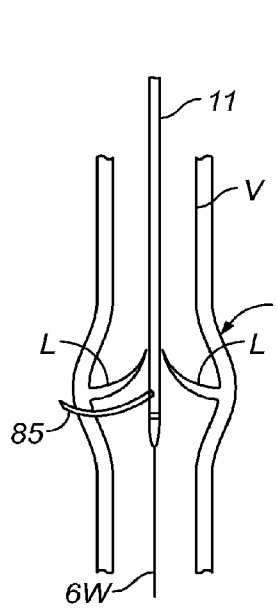
FIGS. 2A-2C show steps in a general method for using a transluminally inserted catheter to deliver a compressor to treat an incompetent venous valve.
Figure 2B:
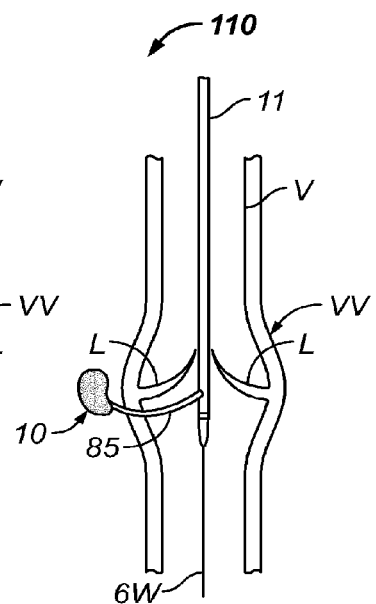
Figure 2C:
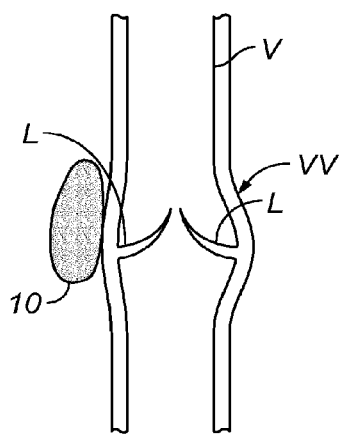

FIGS. 2A through 2C show steps in a general example of a transluminal method of the present invention wherein a tissue penetrating catheter 11 is inserted into the lumen of the vein V in which an incompetent venous valve V V is located. Optionally, a guidewire GW may be inserted first and the catheter 11 may then be advanced over the guidewire GW. A penetrator 85 is advanced from the catheter 11 into tissue adjacent to the venous valve V V. A compressor 10 is then delivered over or through the penetrator 85 such that the compressor 10 becomes implanted or forms a mass at a location outside of and adjacent to the venous valve V V, thereby causing compression of the valve V V in a manner that causes at least one of the valve leaflets L to move toward the other leaflet L. This improves the degree of closure of the leaflets L and the competency of the valve V V. As described in more detail below, the compressor 10 may be a space occupying material and/or one or more implantable device (s)). In some embodiments, the compressor may fully or partially surround the venous valve V V (e.g., a full or partial ring or helical spring may be advanced fully or partially around the valve) while in other embodiments the compressor 10 may be configured so that it is positioned on just one side of the venous valve V V (e.g., next to the base of one of the leaflet(s) and approximately 90 degrees from the valve commissure or plane of separation between the leaflets). As explained in more detail herebelow, the tissue penetrating catheter 11 may be provided with imageable markers and/or an on-board imaging apparatus such as an intravascular ultrasound (IVUS) device to aid the operator in adjusting the longitudinal position and rotation orientation of the catheter 11 prior to advancement of the penetrator 85 to ensure that the penetrator 85 will subsequently advance to the intended location (e.g., next to the base of one of the leaflet(s) and approximately 90 degrees from the valve commissure or plane of separation between the leaflets) and not to some other unintended or less desirable location.

Figure 2D:
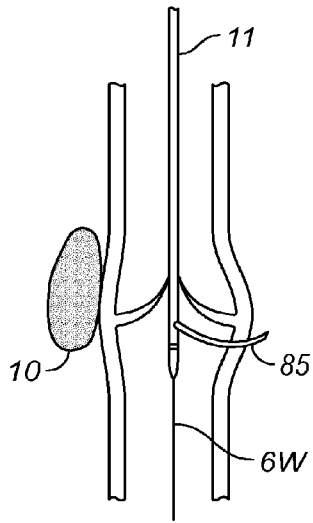
FIGS. 2D-2F show optional additional steps in the general method of preceding FIGS. 2A-2C.
Figure 2E:
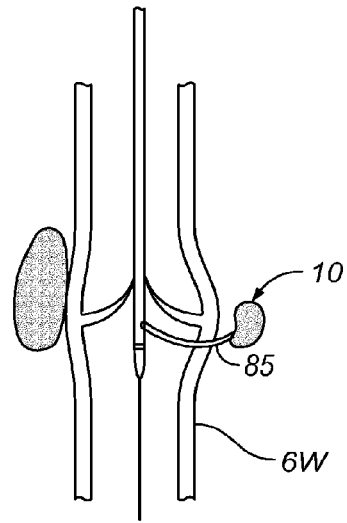
Figure 2F:
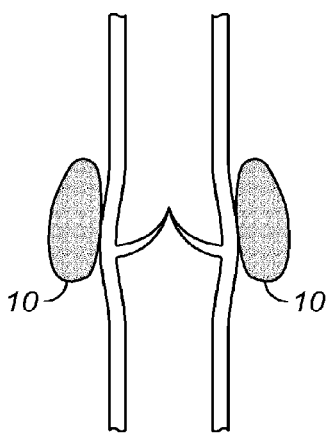

In some embodiments where the compressor 10 is positioned at a discrete location on just one side of the venous valve V V, a single compressor 10 may move the leaflets L together adequately to restore substantial coaptation of the leaflets L, as seen in FIG. 2C. However, in other cases, it may be desirable to deliver one or more additional compressor(s) to other location(s) adjacent to the venous valve V V. Accordingly, FIGS. 2D through 2F show optional additional steps that may be performed to deliver additional compressor(s) 10 to additional location(s) adjacent to the venous valve V V. As shown in FIG. 2D, the tissue penetrating catheter 11 remains positioned within (or if previously removed, has been reinserted into) the lumen of the vein V and the longitudinal position and/or rotational orientation of the catheter 11 has been adjusted as needed to aim the penetrator 85 toward an intended site that, in this example, is diametrically opposite the location at which the first compressor 10 had been implanted (e.g., next to the base of the other leaflet, approximately 90 degrees from the valve commissure or plane of separation between the leaflets and approximately 180 degrees from the previously implanted compressor). After the penetrator 85 has been advanced to this desired location, a second compressor 10 is delivered to the second location as shown in FIG. 2E. This exerts compressive force inwardly on the venous valve V V in a direction opposite the compressive force exerted by the first compressor 10 (delivered in FIG. 2B) and causes the leaflets L to move further together as seen in FIG. 2F.

In any embodiments of the present invention, any suitable technique, such as contrast radiography and/or imaging (e.g., ultrasound imaging) of the valve leaflets L, may be used to determine when the leaflets L have been sufficiently repositioned to once again render the valve V V competent.

In some embodiments, the compressor 10 may comprise injectable space occupying material(s) that may be injected through a lumen in the penetrator 85 or through a small catheter that has been advanced through a lumen of the penetrator 85. Such injectable space occupying material will form a depot or mass at the intended location(s) adjacent to the venous valve V V. The amount of such material(s) injected will be sufficient to exert pressure on the valve V V to cause the desired shift in the position of at least one valve leaflet L and resulting in improved coaptation of the valve leaflets L during closure of the valve. Examples of injectable materials that may be used for this purpose include but are not necessarily limited to; bulking agents, fat, collagens (e.g., collagens from human animal sources), crosslinked collagens (e.g., Zyplast®, Allergan-Inamed, Santa Barbara, Calif.), autologus collagen (Autologen; Collagenesis Inc., Beverly, Mass.); polymethylmethacrylate microspheres suspended in bovine collagen (Artecoll®; Rofil Medical International NV, Breda, The Netherlands), acellular freeze dried human cadaveric dermis (AlloDerm®, LifeCell Corporation, Branchburg, N.J.), micronized acellular freeze dried human cadaveric dermis (Cymetra®, LifeCell Corporation, Branchburg, N.J.), cultured autologous fibroblasts (Isolagen®, Isolagen Technologies, Inc., Exton, Pa.), hyaluronic acid, crosslinked hyaluronic acid (Hylaform® gel; Allergan-Inamed, Santa Barbara, Calif.; and Genzyme Corporation, Cambridge, Mass.), stabilized hyaluronic acid derivatives (Restylane®, Q-Med AB, Uppsala, Sweden), calcium hydroxyl appetite suspension (Radiesse®, Bioform Medical, Inc., San Mateo, Calif.), solubilized elastin peptides with bovine collagen (Endoplast-50®, Laboratoiries Filorga, Paris, France), dextran beads suspended in hylan gel (Reviderm®, Rofil Medical International NV, Breda, The Netherlands), silicones (e.g., high-viscosity liquid silicone such as Adatosi-5000™ and Silikon-1000™, Dow Corning, Midland Mich.), poly-L-lactic acid (Sculptra®, Dermik Aesthetics, Berwyn, Pa.), expanded polytetrafluoroethylene (e-PTFE) (e.g., SoftForm™ from Collagen Aesthetics, Inc., acquired by Allergan-Inamed, Santa Barbara, Calif. or Advanta™ from Atrium Medical Corporation, Hudson, N.H.), etc.

In other embodiments, the compressor 10 may comprise one or more implantable device(s) which exert pressure on the venous valve V V. Such implantable device(s) may comprise one or more relatively simple space occupying articles or apparatus such as, for example, beads, balls, filament(s), strand(s), coils, suture material, etc. Or, such implantable device(s) may comprise and expandable implant such as a stent, an expandable cage, expandable cylinder, expandable ball, other expandable structures, implantable balloons, implantable balloons filled with solid, liquid, gaseous or gelatinous material, implantable tissue expanders, etc.

Alternatively, the compressor 10 may comprise implantable device(s) such as a ring, partial ring, helix or other member that may be advanced around or partially around the venous valve V V and caused to exert inward pressure on the venous valve V V.

Some non-limiting examples of implantable devices that may be used in this invention are shown in FIGS. 5A-6G and will be discussed in detail elsewhere in this patent application.

FIGS. 3A-3G show details of one example of a tissue penetrating catheter 11 that may be used for transluminal delivery of the compressor 10. This tissue penetrating catheter 11 includes an elongated catheter body 13 having a proximal end 15, a distal end 17, a handle 19 and a hub 21 coupled to the proximal end of the catheter body 15 and to the handle. The handle 19 may also serve as a controller for use in advancing and retracting the penetrating instrument, such as a tissue penetrator 85 described more fully below.

The Catheter Body

Figure 3:
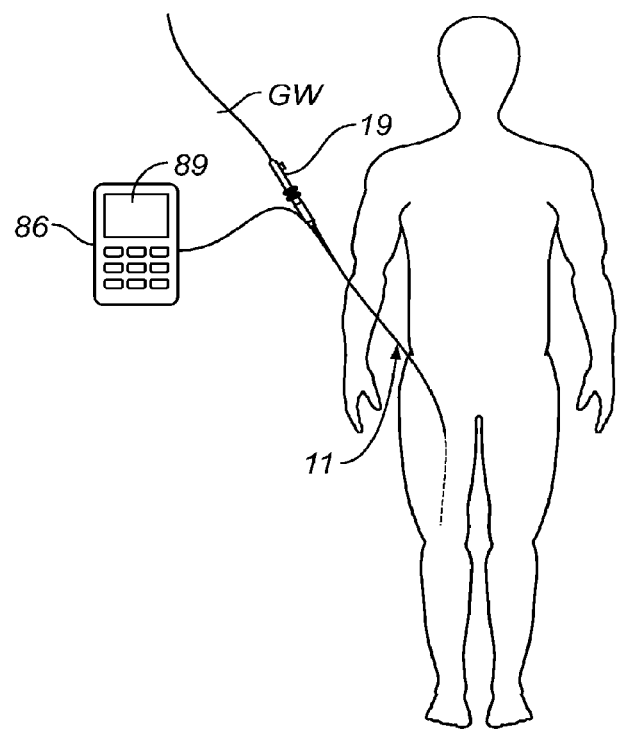
FIG. 3 is schematic illustration showing a tissue penetrating catheter system operatively inserted into a human patient and being used to perform a venous valve treatment method of the present invention.
Figure 3A:
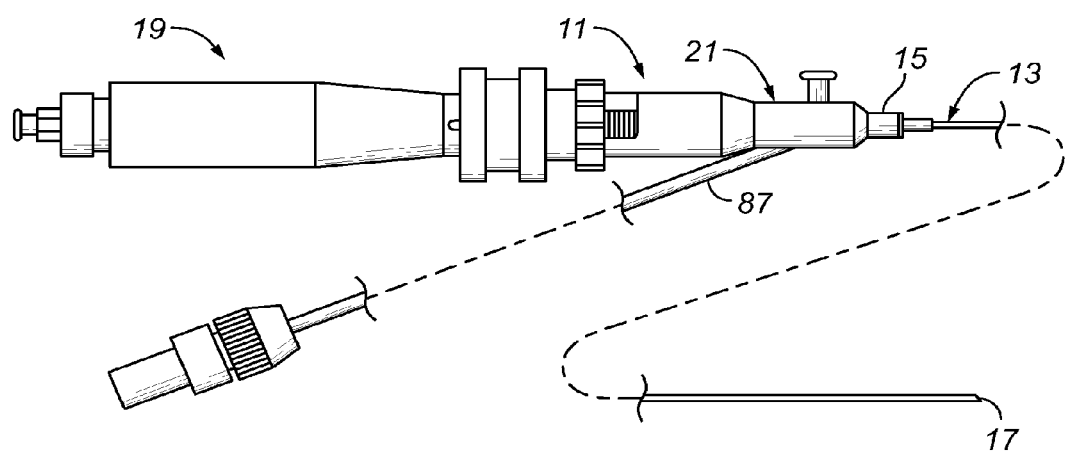
FIG. 3A is a side view of the tissue penetrating catheter device shown in FIG. 3.

The catheter body 13 includes a relatively rigid proximal section 23 which may be constructed, for example, of a metal hypo tube and an elongated flexible distal section or region suitably joined to and extending distally from the proximal section. A hand piece 19 is attached to the proximal end of the proximal section 23, as shown. In the preferred embodiment for performing procedures in the veins of the leg, the hand piece 19 and proximal section 23 are approximately 150 cm in length. The flexible distal section may incorporate a reinforcement member such as a wire braid 400 as shown in FIG. 3D and, which in the example shown may be approximately 130 cm in length. This braid 400 may terminate approximately 3 cm from the distal end 17.

In this example, the catheter body 13 has a penetrator lumen 27 that terminates distally at an exit location or exit port 29 on the side wall of the catheter. The penetrator lumen 27 extends proximally from the exit port 29 to the proximal end 15 of the catheter body 13 and communicates with the interior of the handle 19 through the hub 21. The penetrator lumen 27 contains the tissue penetrator 85, which is advanceable from the catheter body 13 through the wall of blood vessel in which the catheter body 13 is positioned and to a desired location outside of and adjacent to the incompetent venous valve. The exit port 29 is preferably located a short distance proximal to the distal tip 17. A radiopaque marker may be mounted on the lumen 27 adjacent the exit port 29.

In some applications, the compressor 10 may comprise a space occupying substance that is formed by the mixture or chemical reaction of two or more component substances. In such applications, the penetrator 85 or other injector device may have two or more lumens may be used to inject the component substances so that they become combined in situ at the implantation site or within the injection device shortly before the resultant component mixture enters the implantation site. Examples of other multiple-component injector devices that may be used for injection of multiple components in this manner include but are not necessarily limited to those described in U.S. Provisional Patent Application No. 60/878,527 filed Jan. 3, 2007 and in U.S. patent application Ser. No. 11/426,219 filed Jun. 23, 2006 (published as United States Published Patent Application 2007-0014784), which claims priority to U.S. Provisional Patent Application Nos. 60/693,749 filed Jun. 23, 2005 and 60/743,686 filed Mar. 23, 2006, the entire disclosures of each such patent application being expressly incorporated herein by reference.

The catheter body 13 may also have a guidewire lumen 35 which extends to the distal end 17 of the catheter body 13. In this embodiment, the guidewire lumen 35 extends proximally to an inlet port 37 on the catheter side wall adjacent to the proximal section 23. The catheter body also has a lead lumen 39 for a purpose described below.

In this example, the catheter includes a tapered distal tip section 55 of soft, flexible, biocompatible material and exit port 29 is spaced slightly proximally of shoulder 57.

Imaging Transducer

In the particular embodiment of the penetrating catheter 11 shown, an on-board imaging transducer 81 is positioned in the distal tip section 55 just distal to shoulder 57. In this embodiment, the imaging transducer 81 comprises a phased array transducer (e.g, an intravascular ultrasound transducer or IVUS) operative to image 360° about the catheter 11. This imaging transducer 81 comprises an annular array of individual crystals or elements coupled to a multiplex circuit which is within the catheter body 13 adjacent the shoulder 57. The multiplex circuit is in turn coupled to leads which extend through the lead lumen 39 and a port or sidearm 87 of the hub 21 to an imaging console 86. When activated, the imaging transducer 81 emits ultrasound signals and receives back echos or reflections which are representative of the nature of the surrounding environment. The imaging transducer 81 provides an imaging signal from which an image of the surrounding structures can be created by signal processing apparatus located in an imaging console having a display screen 89. A suitable phased array transducer as well as the accompanying circuitry and imaging console may be obtained commercially from Volcano Corporation of Rancho Cordova, Calif. or Intravascular Research Limited (United Kingdom).

Orientation Marker

Figure 3F:
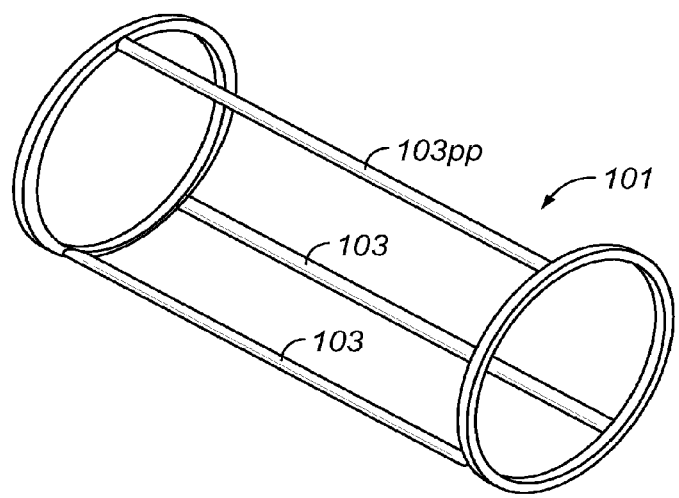
FIG. 3F is a perspective view of the marker structure of the tissue penetrating catheter shown in FIGS. 3A-3E.
Figure 3G:
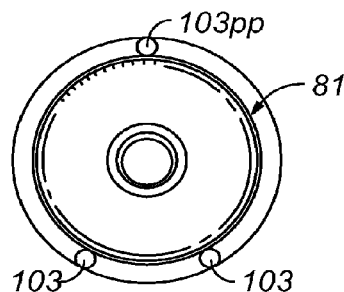
FIG. 3G is a non-fragmented cross sectional view through line 3G-3G of FIG. 3B.
Figure 4A:
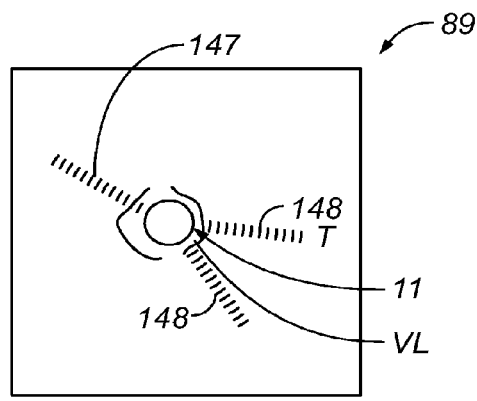
FIG. 4A shows an example of an intravascular ultrasound image that the operator may see when the tissue penetrating catheter has been positioned within the lumen of the affected vein near the venous valve to be treated, but wherein the tissue penetrating catheter is not in the proper rotational orientation to cause the projected penetrator path to be directed toward the intended target location (T) at which the compressor is to be delivered.
Figure 4B:
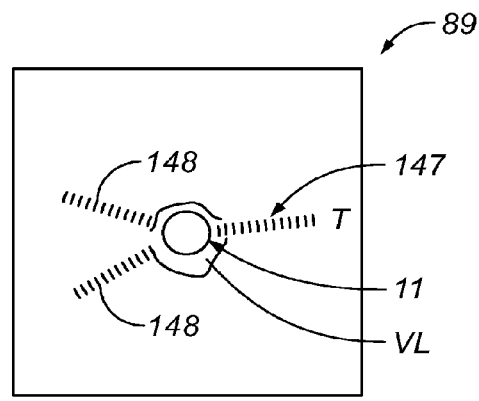
FIG. 4B shows an example of an intravascular ultrasound image that the operator may see after the rotational orientation of the tissue penetrating catheter of FIG. 4A has been adjusted so that the projected penetrator path is directed toward the intended target location (T) at which the compressor is to be delivered.

An imageable marker structure 101 is fixedly mounted on the catheter body 13 in a known circumferential orientation relative to the exit port 29. As seen in FIG. 3F, this marker structure 101 is generally in the form of a cage having three longitudinal members 103 and 103pp. As seen in FIG. 3G, this marker structure 101 is mounted on the catheter such that the imaging transducer 81 is within the longitudinal members 103 and 103pp. The longitudinal members 103 and 103pp are disposed at circumferentially spaced apart locations. Each of these longitudinal members creates an image 147 or 148 on the ultrasound display 89, as illustrated in FIGS. 4A and 4B. One of the longitudinal members 103pp is positioned at a circumferential position that is axially aligned with the exit port 29 or otherwise positioned to be indicative of the trajectory on which the tissue penetrator 85 will advance from the catheter body 13 and is designated as the penetrator path indicating member 103pp. As seen on FIGS. 4A and 4B and described more fully herebelow, the ultrasound image 147 created by this penetrator path indicating member 103PP is distinguishable from the images 148 created by the other two strut members 103, thereby providing to the operator an indication of the projected path on which the penetrator 85 will subsequently advance from the catheter body 13.

More specifically, FIGS. 4A and 4B are an illustration of what the operator may see on the display screen 89 during performance of a trans-luminal method of the present invention using the particular tissue penetrating catheter 11 shown in FIGS. 3A-3G. Specifically, in FIG. 4A, the tissue penetrating catheter 11 has been inserted into the vein and advanced to a position where the distal end of the catheter 11 is within or protruding slightly through an incompetent venous valve V V. On the image display 89, one can see the surrounding wall of the vein in which the catheter 11 is positioned as well as an indication of the target location T to which it is desired to advance the penetrator 85. The penetrator path indicator 147 (i.e., the ultrasound image created by the penetrator path indicating member 103pp) is visually distinguishable from the images 148 created by the other longitudinal members 103 of the marker structure 101. In the example of FIG. 4A, this penetrator path indicator 147 is not directed toward the target area T. Thus, if the penetrator 85 were to be advanced from the catheter body 13 at this time the penetrator 85 would not travel in the target area T. In view of this, the operator may rotate the catheter 11 until the penetrator trajectory image 147 leads to the target area T, as shown in FIG. 4B. Thereafter, the penetrator 85 may be advanced with reasonable assurance that it will advance toward the target location T and not in some other radial direction.

It will be appreciated that, as an alternative to the use of the marker structure 101, the imaging transducer 81 could be mounted in a fixed position and a selected one (or selected ones) of the individual imaging elements (e.g., crystals) of the phased array may be selected as being in longitudinal alignment with the exit port 29 or otherwise located so as to be indicative of the trajectory on which the penetrator 85 will advance from the catheter body 13. This selected imaging element(s) shall be referred to herein as the "penetrator-path-indicating imaging element(s)." The imaging console 86 may include a computer or processor that is programed to display on the imaging display a marking (e.g., a vertical line or other suitable making) that is in aligned with the radial location of the penetrator-path-indicating imaging element(s). Thus, such marking will serve as a visual indicator of the trajectory that will be followed by the tissue penetrator 85 as it is advanced from the catheter body 13. It will be appreciated by those of skill in the art that this marking may be created on the imaging display screen electronically (e.g., as an illuminated or colored line on the image) or it may be physically marked on the screen (e.g., by felt tipped marker or other suitable marking material or apparatus such as a template). In such embodiments, the operator may rotate the catheter until the marking (e.g., vertical line) passes directly through the image of the venous valve to be repaired, thus indicating to the operator that when the tissue penetrator 85 is subsequently advanced from the exit port 29, it will advance toward the intended implantation site adjacent to the intended venous valve, and not in some other radial direction.

Also, as an alternative to the use of the marker structure 101 and any on-board imaging transducer 81, the catheter may include suitable radiographic marking to allow the operator to rotationally adjust and radially orient the catheter using fluoroscopy or other radiographic imaging.

FIGS. 5A and 5B show a method wherein the above described tissue penetrating catheter device 11 is used to implant a valve compressing device 10a which comprises a helical spring that advances around the venous valve V V and exerts inward pressure on the valve V V to move the valve leaflets L toward each other. In this example, a guidewire GW is initially inserted through an introducer that has been placed in the femoral vein and the guidewire is advanced in the retrograde direction through the vein V and through the venous valve V V to be treated. The tissue penetrating catheter 11 is then advanced over the guidewire GW to a position where the penetrator outlet opening of the catheter 11 (see item 29 on FIG. 3B) is located just below the base of the valve leaflets L. The longitudinal positioning of the catheter 11 may be guided or confirmed by x ray, fluoroscopy or other suitable means through radiographic visualizations of markers(s) or other radiopaque structures of the catheter 11 (e.g., the retracted penetrator 85 or its metal housing). Thereafter, as described above, the catheter 11 may be rotated to its desired rotational orientation so that the penetrator 85 is effectively aimed at the intended target location. For example, if the catheter 11 is equipped with the optional imaging transducer 81, the imaging transducer will then be actuated and the operator, while viewing an image from the imaging transducer 81, will rotate the catheter 11 as needed until the penetrator path indication 147 is aligned with the location where it is desired to initially introduce the compressor device 10a. As seen in FIG. 5B, after the catheter 11 has been positioned and rotationally oriented so that the penetrator 85 is effectively aimed at the desired location, the penetrator 85 is advanced to the desired location. In this example, the penetrator 85 comprises a hollow needle having a lumen. Thereafter, the compressor device 10a, which in this case comprises an elastic or superelastic wire that it set to a desired helical configuration, is advanced through the lumen of the penetrator 85 such that it exits the distal end of the penetrator and advances on a helical path around the venous valve V V as shown. In some embodiments, the compressor device 10a may be formed at least partially of a shape memory material, such as a nickel-titanium alloy which has been processed according to techniques well known in the art so that, following implantation, as it warms to body temperature the device 10a closes or tightens around the valve, thereby inwardly compressing the valve. Alternatively, in some embodiments, the compressor device 10a may be pre-sized for the vein diameter so that different sized vessels will receive different diameter wires. The valve diameter may be measured by known imaging techniques and the desired size of wire may be loaded into the delivery system, similar to stent sizing techniques currently used in the art.

It will be appreciated that, as an alternative to this helical device 10a, other devices that surround or partially surround the valve V V, such as rings or partial rings, may also be used in a manner similar to that described here.

FIGS. 6A-6D show an example of a compressor 10b which comprises an implantable device that is positionable at a discrete location adjacent to the venous valve V V and expands to exert pressure on the valve V V. This embodiment of the compressor 10b may be either self expanding or pressure expandable. As shown in FIG. 6A, the tissue penetrating catheter 11 is inserted, longitudinally positioned and rotationally oriented as described above with respect to FIG. 5A. Thereafter, the penetrator 85 is advanced to the location where implantation of the compressor 10b is desired (e.g., outside of the valve next to the base of one of the leaflet(s) and approximately 90 degrees from the valve commissure or plane of separation between the leaflets). Thereafter, the compressor is delivered from, over or through the penetrator 85 such that it expands and becomes implanted adjacent to the venous valve V V as shown in FIG. 6B. Optionally, one or more additional compressor(s) 10b may also be delivered to other locations adjacent to the valve V V. In embodiments where the compressor device 10b is self-expanding, it may be mounted on the outer surface of the penetrator 85 and may be constrained by a sheath, clips, ties or other constraint apparatus during advancement to the implantation site. Thereafter, the constraint apparatus may be removed or deactivated, thereby allowing the compressor device 10b to self-expand. Alternatively, where the device 10b is self-expanding, it may be delivered through (e.g., pushed through) the lumen of a hollow penetrator 85 while in a collapsed state and allowed to expand in situ as it exits out of the distal end opening of the hollow penetrator 85. Examples of small self-expanding stents or other self expanding devices that may be used for this purpose include but are not limited to the COMPLETE™ stent available from Medtronic Vascular, Inc. Santa Rosa, Calif. as well as small self expanding stents available from Johnson & Johnson Cordis, Boston Scientific, eV3 and others. In embodiments where the compressor device 10b is pressure expandable, the penetrator 85 may have a balloon B or other expander apparatus mounted on its outer surface and the compressor device 10b may be initially crimped or otherwise mounted over that balloon B or expander, as shown in FIG. 6C, so that, after the penetrator has been advanced, the balloon B or other expander apparatus may be expanded, thereby causing the compressor 10b to plastically deform to an expanded configuration. Alternatively, the compressor device 10b may be initially crimped or otherwise mounted on a delivery catheter C that has a balloon B or other expander apparatus thereon and that delivery catheter C may then be advanced through the lumen of a hollow penetrator 85 and out of its distal end, as shown in FIG. 6D. Thereafter, the balloon B or other expander may be expanded causing the compressor 10b to deform to its expanded configuration. Examples of small balloon-expandable, plastically deformable stents or other devices that may be used as the compressor device 10b and delivery catheters therefore include the Guidant MULTI-LINK RX PIXEL® Coronary Stent System (Abbott Vascular, Inc., Santa Clara, Calif.) and the Micro-Driver® Coronary Stent System (Medtronic Vascular, Inc., Santa Rosa, Calif.). Another small balloon catheter device that may be used for delivery and expansion of a pressure expandable compressor device 10b is a balloon equipped guidewire having a balloon that has a deflated diameter of about 0.028 inch and a fully inflated diameter of about 5.5 mm (GuardWire® Temporary Occlusion System, Medtronic Vascular, Inc., Santa Rosa, Calif.).

After the compressor 10b has been expanded sufficiently to exert the desired pressure on the venous valve, the balloon or expander may be deflated or collapsed, the penetrator 85 (and any deliver catheter used) may be retracted into the penetrating catheter 11, and the penetrating catheter 11 may be removed, leaving the compressor device(s) 10b in place, as shown in FIG. 6B.

FIGS. 6E-6G show non-limiting examples of some expandable compressor devices 10b that could be used in this invention. For example, FIG. 6E shows an expandable, substantially cylindrical mesh tube 10b-1 in the nature of a stent that may be self-expanding or pressure expandable. FIGS. 6F and 6G show an implantable spring device formed of a zig-zag member which forms and indented ring 10b-2. The indented side of this device may be positioned adjacent to the venous valve V V so that it extends partially around the valve. This device 10b-2 may also be either self expanding or pressure expandable.

Any delivery catheter that is to be advanced out of the penetrator 85 may itself have a sharp distal tip to facilitate its desired advancement through tissue to the desired implantation site.

It will be appreciated that, in embodiments where the compressor 10 is delivered transluminally using one or more catheters, it will be desirable to insert and remove the catheters in a manner that allows the procedure to be performed without causing damage or further damage to any venous valve leaflets L, including the leaflets of the valve on which the procedure is being performed. To accomplish this, the tissue penetrating catheter 11 and/or other catheter(s) used to perform the procedure, will be sufficiently small in diameter and of a configuration that is sufficiently atraumatic to be advanced through venous valves V V without causing substantial damage to the valve leaflets L. Additionally, a lubricious coating, such as a hydrogel coating, may be applied to the outer surfaces of the catheter(s) to limit friction on the leaflets L as the catheter(s) pass between the leaflets L. Also, in some cases, rather than entering the venous vasculature though a femoral venipuncture site and advancing the catheter(s) in the retrograde direction (i.e., opposite normal venous blood flow), it may be desirable to enter the venous vasculature percutaneously or by cut-down at a site that is distal to the venous valve to be treated and then advance the catheter(s) through venous valves in the direction of normal venous blood flow, thereby causing the valve leaflets L to separate in a natural fashion.

Alternatively, as shown in FIG. 7, it is possible to insert the penetrating catheter 11 into the arterial vasculature and to advance the catheter 11 into an artery A near the venous valve V V to be treated, thereby avoiding any potential for damage of venous valves by advancement of the catheter 11. The orientation apparatus of the catheter may then be used to essentially aim the penetrator 85 at the venous valve V V in the adjacent vein V and the penetrator 85 may then be advanced to a location outside of but near the venous valve VV, as shown. Thereafter, a compressor 10 may be delivered over, from or through the penetrator 85 as described above.

It is to be further appreciated that, in some embodiments of the invention, the compressor device may be designed to initially advance fully or partially around the exterior of the venous valve so as not to puncture into the valve itself and to subsequently contract to a smaller diameter or cross-dimension so as then compress the valve inwardly thereby improving coaptation of the valve leaflets. To accomplish this, the compressor may initially have a first curved shape and may subsequently contract to more tightly curved or coiled shape. For example, FIGS. 8A-8D show an embodiment of a compressor device 10f which comprises a tubular catheter 92 having a clip member 94 connected to its distal end by way of a releasable connection 98. A lumen or central passage extends longitudinally though the clip member 94 in alignment with the lumen of the catheter 92. An elastic or super elastic wire mandrel 96 is initially inserted through the lumen of the catheter 92 and into the lumen of the clip member 94. This system is then advanced through the lumen of the penetrator 85. As the clip member 94 advances out of the distal end of the penetrator 85, it assumes the first curved configuration of the wire mandrel (shown in FIG. 8C) which allows it to advance around the exterior of the venous valve VV without penetrating into the venous valve in the manner shown in FIG. 8A. Thereafter, the wire mandrel is removed, allowing the clip member 94 to contract to its more tightly coiled shape (seen in FIG. 8D) thereby compressing the venous valve VV to improve coaptation of the valve leaflets L. Thereafter, the releasable connection is released, the catheter portion 92 is retracted back into the penetrator 85, the penetrator 85 is retracted back into the tissue penetrating catheter 11 and the tissue penetrating catheter 11 is removed, leaving just the clip member 94 in place as seen in FIG. 8B. Various types of releasable connections useable in this system are known in the art of medical catheter-based device design including connections that separate by force, melt, thermally degrade, dissolve, release by hydraulic or fluid pressure, or otherwise separate.

FIGS. 9 and 9A show yet another embodiment of a venous valve compressor device 10g that has a first configuration that allows it to advance around the exterior of a venous valve and, thereafter, contracts to a second configuration that causes compression of the venous valve to improve closure of the valve leaflets. This compressor 10g comprises a helical wire 98 that is biased to the second configuration (e.g., a tight helical or curved configuration) and a biodegradable polymer covering 100 on the wire that initially overcomes the bias of the wire 98 so that the wire can only curve to the first configuration (e.g., a looser helical or curved configuration). Initially, this device 10g may be advanced around a venous valve in the same manner as shown in FIGS. 5A and 5B and described above. Thereafter, as the device 10g remains implanted, the biodegradable covering 100 will degrade thereby allowing the wire 98 to contract around the venous valve to cause the desired compression of the venous valve.

FIGS. 10 and 10A show yet another approach using a venous valve compressor system 10h that comprises a biodegradable spacer 102 that is initially placed around the venous valve VV surrounded by a helical wire compressor 104. Such a spacer 102 may comprise a biodegradable polymer that is delivered through the lumen of the penetrator 85 of the tissue penetrating catheter and allowed to solidify in place or any other suitable type of biodegradable material that may be installed around the venous valve. The helical wire compressor 104 is biased to a curve or coiled diameter that initially cannot compress the spacer 102 but will later contract to compress the venous valve after the biodegradable spacer 102 has degraded. Initially, the wire compressor 104 is advanced around the spacer 102 and the spacer 102 prevents the distal tip of the wire compressor 104 from penetrating into the venous valve as it advances around the spacer 102 as seen in FIG. 10. In time, the spacer 102 biodegrades, allowing the helical wire compressor 104 to contract to its smaller diameter, thereby compressing the venous valve VV and improving closure of the valve leaflets Las seen in FIG. 10A.

It is to be further appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method or process are described, listed or claimed in a particular order, such steps may be performed in any other order unless to do so would render the embodiment or example not novel, obvious to a person of ordinary skill in the relevant art or unsuitable for its intended use. All reasonable additions, deletions, modifications and alterations are to be considered equivalents of the described examples and embodiments and are to be included within the scope of the following claims.

What is claimed is:

1. A method for improving function of a venous valve that comprises valve leaflets, said venous valve being located in a vein that has a wall and a lumen, said method comprising the steps of:
    positioning, within the lumen of the vein in which the venous valve is located or within the lumen of another blood vessel that has a wall and is located near the venous valve, a tissue penetrating catheter that has a penetrator that is advanceable from the catheter;
    advancing the penetrator from the tissue penetrating catheter through the wall of the vein or other blood vessel in which the catheter is positioned toward a first location outside of the vein;
    delivering a balloon catheter or balloon guidewire having an inflatable balloon with a first pressure-expandable compressor initially mounted on the balloon of the balloon catheter or balloon guidewire while in a non-expanded configuration, through the penetrator to said first location,
    inflating the balloon of the balloon catheter or balloon guidewire to expand said first pressure-expandable compressor at said first location to a desired expanded size;
    withdrawing the balloon catheter or balloon guidewire leaving the first compressor in place at the first location;
    retracting the penetrator;
    repositioning the tissue penetrating catheter;
    advancing the penetrator from the tissue penetrating catheter through the wall of the vein or other blood vessel in which the catheter is positioned toward a second location outside of the vein, wherein the second location is on an opposite side of the venous valve relative to the first location;
    delivering a balloon catheter or balloon guidewire having an inflatable balloon with a second pressure-expandable compressor initially mounted on the balloon of the balloon catheter or balloon guidewire while in a non-expanded configuration, through the penetrator to said second location;
    inflating the balloon of the balloon catheter or balloon guidewire to expand the second compressor at said second location to a desired expanded size;
    withdrawing the balloon catheter or balloon guidewire leaving the second compressor in place at the second location;
    retracting the penetrator; and
    removing the tissue penetrating catheter,
    wherein the first and second compressors expanded at the first and second locations to the desired expanded sizes cause sufficient inward compression of the wall of the vein in the area of the venous valve to improve closure of the venous valve leaflets.

2. A method according to claim 1 wherein the tissue penetrating catheter is equipped with orientation apparatus useable to determine a projected penetrator path on which the penetrator will subsequently advance from the catheter and wherein the method further comprises the steps of:
    using the orientation apparatus to determine a projected penetrator path relative to the first location or the second location; and
    adjusting the rotational orientation of the catheter as needed so that the projected penetrator path indicates that the penetrator will advance toward said first location or said second location.

3. A method according to claim 1 wherein the tissue penetrating catheter is positioned in the vein in which the venous valve is located.

4. A method according to claim 1 wherein each balloon has a deflated diameter of about 0.028 inch and a fully inflated diameter of about 5.5 mm.

5. A method according to claim 1 wherein the tissue penetrating catheter has a lubricious outer coating.

6. A method according to claim 1 wherein the tissue penetrating catheter is inserted proximal to the venous valve and advanced through one or more veins in the direction opposite normal venous blood flow.

7. A method according to claim 1 wherein the tissue penetrating catheter is inserted distal to the venous valve and advanced through one or more veins in the direction of normal venous blood flow.

8. A method according to claim 1 further comprising the step of using contrast radiography, ultrasound or other imaging to determine during performance of the method when the venous valve leaflets have been sufficiently repositioned to improve closure.

9. A method for improving function of a venous valve that comprises valve leaflets, said venous valve being located in a vein that has a wall and a lumen, the method comprising the steps of:
   positioning, within the lumen of the vein in which the venous valve is located or within the lumen of another blood vessel that has a wall and is located near the venous valve, a tissue penetrating catheter that has a penetrator that is advanceable from the catheter, said penetrator having a balloon mounted on an outer surface of the penetrator and a first compressor mounted on the balloon in a non-expanded configuration while the balloon is deflated;
   advancing the penetrator with the balloon and non-expanded first compressor through the wall of the vein or other blood vessel in which the catheter is positioned toward a first location outside of the vein;
   using the balloon to expand the first compressor;
   withdrawing the penetrator and the balloon, leaving the first compressor in place at the first location;
   causing a second compressor to be placed, in a non-expanded configuration, on the balloon of the penetrator while the balloon is deflated;
   repositioning the tissue penetrating catheter;
   again advancing the penetrator with the balloon and the non-expanded second compressor from the tissue penetrating catheter through the wall of the vein or other blood vessel in which the catheter is positioned toward a second location, wherein the second location is on an opposite side of the venous valve relative to the first location;
   using the balloon to expand the second compressor;
   retracting the penetrator and the balloon leaving the second compressor in place at the second location; and
   removing the tissue penetrating catheter.

10. A method for improving function of a venous valve that comprises valve leaflets, said venous valve being located in a vein that has a wall and a lumen, said method comprising the steps of:
   positioning, within the lumen of the vein in which the venous valve is located or within the lumen of another blood vessel that has a wall and is located near the venous valve, a tissue penetrating catheter that has a penetrator that is advanceable from the catheter;
   advancing the penetrator from the tissue penetrating catheter through the wall of the vein or other blood vessel in which the catheter is positioned toward a first location outside of the vein;
   delivering an expander apparatus and a first compressor through the penetrator to the first location, wherein the expander apparatus is mounted on a delivery catheter that is advanced through the penetrator, wherein the delivery catheter has a sharp tissue penetrating distal tip;
   using the expander apparatus to expand the first compressor;
   withdrawing the expander apparatus leaving the first compressor in place at the first location;
   retracting the penetrator;
   repositioning the tissue penetrating catheter;
   again advancing the penetrator from the tissue penetrating catheter through the wall of the vein or other blood vessel in which the catheter is positioned toward a second location outside of the vein, wherein the second location is on an opposite side of the first location relative to the venous valve;
   delivering an expander apparatus and a second compressor through the penetrator to the second location, wherein the expander apparatus comprises a delivery catheter with a sharp tissue penetrating distal tip;
   using the expander apparatus to expand the second compressor;
   withdrawing the expander apparatus leaving the second compressor in place at the second location;
   retracting the penetrator; and
   removing the tissue penetrating catheter,
   wherein the first and second compressors expanded at the first and second locations to the desired expanded sizes cause sufficient inward compression of the wall of the vein in the area of the venous valve to improve closure of the venous valve leaflets.

* * * * *